United States Patent
Kita (10) Patent No.: US 11,030,911 B2
(45) Date of Patent: Jun. 8, 2021

(54) ELECTRONIC APPARATUS, NOTIFICATION METHOD, AND COMPUTER-READABLE STORAGE MEDIUM

(71) Applicant: CASIO COMPUTER CO., LTD., Tokyo (JP)

(72) Inventor: Kazunori Kita, Tokyo (JP)

(73) Assignee: CASIO COMPUTER CO., LTD., Tokyo (JP)

(*) Notice: Subject to any disclaimer, the term of this patent is extended or adjusted under 35 U.S.C. 154(b) by 191 days.

(21) Appl. No.: 15/427,256

(22) Filed: Feb. 8, 2017

(65) Prior Publication Data

US 2017/0282012 A1 Oct. 5, 2017

(30) Foreign Application Priority Data

Mar. 31, 2016 (JP) .............................. JP2016-072798
Sep. 23, 2016 (JP) .............................. JP2016-186164

(51) Int. Cl.
*G09B 19/00* (2006.01)
*G09B 5/02* (2006.01)
(Continued)

(52) U.S. Cl.
CPC ............ *G09B 5/02* (2013.01); *A61B 5/02438* (2013.01); *A61B 5/4866* (2013.01); *A61B 5/681* (2013.01);
(Continued)

(58) Field of Classification Search
CPC ........................ G09B 19/0092; A61B 5/4875
See application file for complete search history.

(56) References Cited

U.S. PATENT DOCUMENTS

2002/0028988 A1  3/2002 Suzuki et al.
2005/0070778 A1* 3/2005 Lackey ................ A61B 5/0537
                                                      600/366
(Continued)

FOREIGN PATENT DOCUMENTS

CN       103565648 A    2/2014
JP       2001-327472 A  11/2001
(Continued)

OTHER PUBLICATIONS

First Office Action dated Sep. 21, 2018 received in Chinese Patent Application No. CN 201710100108.1 together with an English language translation.
(Continued)

*Primary Examiner* — Omkar A Deodhar
(74) *Attorney, Agent, or Firm* — Scully Scott Murphy & Presser (57) ABSTRACT

A mobile terminal includes a sensor information acquisition unit, a state calculation unit, and an output control unit. The sensor information acquisition unit successively acquires bio-information relating to a subject. The sensor information acquisition unit acquires activity information relating to activity of the subject. The state calculation unit estimates a physical condition of the subject based on the bio-information acquired and the activity information acquired. The output control unit controls the output unit to perform a notification of information based on the physical condition of the subject estimated.

13 Claims, 5 Drawing Sheets

(51) Int. Cl.
*A61B 5/00* (2006.01)
*A61B 5/024* (2006.01)
*G16H 20/30* (2018.01)
*G16H 50/50* (2018.01)
*G16H 40/63* (2018.01)
*A61B 5/11* (2006.01)
*A61B 5/01* (2006.01)
*A61B 5/021* (2006.01)

(52) U.S. Cl.
CPC ........ *A61B 5/7271* (2013.01); *G09B 19/0092* (2013.01); *G16H 20/30* (2018.01); *G16H 40/63* (2018.01); *G16H 50/50* (2018.01); *A61B 5/01* (2013.01); *A61B 5/021* (2013.01); *A61B 5/1112* (2013.01); *A61B 2503/10* (2013.01); *A61B 2560/0242* (2013.01)

(56) References Cited

U.S. PATENT DOCUMENTS

| | | | | |
|---|---|---|---|---|
| 2006/0122474 | A1* | 6/2006 | Teller | A61B 5/02055 600/300 |
| 2007/0048224 | A1* | 3/2007 | Howell | A61B 5/4277 424/9.1 |
| 2008/0064016 | A1* | 3/2008 | Aruffo | G09B 19/0092 434/262 |
| 2010/0003647 | A1* | 1/2010 | Brown | G09B 19/0092 434/127 |
| 2012/0083711 | A1* | 4/2012 | Goldstein | A61B 5/4277 600/573 |
| 2012/0143019 | A1* | 6/2012 | Russell | A61B 5/0205 600/301 |
| 2014/0017644 | A1 | 1/2014 | Edman et al. | |
| 2014/0221792 | A1* | 8/2014 | Miller | A61B 5/4875 600/309 |
| 2014/0273925 | A1* | 9/2014 | Burgett | H04W 4/027 455/405 |
| 2014/0372045 | A1* | 12/2014 | Keski-Pukkila | A61B 5/6887 702/19 |
| 2015/0042468 | A1* | 2/2015 | White | G16H 20/30 340/539.11 |
| 2015/0073723 | A1* | 3/2015 | Mulligan | G16H 50/30 702/19 |
| 2015/0093725 | A1* | 4/2015 | Baarman | G06F 19/3475 434/127 |
| 2015/0182797 | A1* | 7/2015 | Wernow | G06F 19/3418 434/247 |
| 2015/0196251 | A1* | 7/2015 | Outwater | A61B 5/4875 600/301 |
| 2015/0216471 | A1* | 8/2015 | Goldstein | A61B 10/0051 600/373 |
| 2016/0022209 | A1* | 1/2016 | Fraisl | A45F 3/16 600/590 |
| 2016/0038037 | A1* | 2/2016 | Kovacs | A61B 5/0205 600/301 |
| 2016/0117937 | A1* | 4/2016 | Penders | G06F 16/9535 434/236 |
| 2016/0128625 | A1* | 5/2016 | Lee | A61B 5/486 600/509 |
| 2016/0220184 | A1* | 8/2016 | Manion | A61B 5/4875 |
| 2017/0000348 | A1* | 1/2017 | Karsten | G06F 19/3418 |
| 2017/0084195 | A1* | 3/2017 | Roberts | G09B 19/0092 |
| 2017/0216667 | A1* | 8/2017 | Garvey | G09B 19/0092 |
| 2018/0110415 | A1* | 4/2018 | Sasahara | G09B 19/0038 |

FOREIGN PATENT DOCUMENTS

| | | |
|---|---|---|
| JP | 2002-330933 A | 11/2002 |
| JP | 2006-320735 A | 11/2006 |
| JP | 2013-132516 A | 7/2013 |
| JP | 2014-074976 A | 4/2014 |
| JP | 2014-208314 A | 11/2014 |
| JP | 2015-181708 A | 10/2015 |
| JP | 2015-189740 A | 11/2015 |

OTHER PUBLICATIONS

Notice of Reasons for Refusal dated Jul. 28, 2020 received in Japanese Patent Application No. JP 2016-186164 together with an English language translation.

Notice of Reasons for Refusal dated Feb. 24, 2021 received in Japanese Patent Application No. JP 2016-186164 together with an English language translation.

* cited by examiner

FIG. 5 under compression. # ELECTRONIC APPARATUS, NOTIFICATION METHOD, AND COMPUTER-READABLE STORAGE MEDIUM This application claims the benefit of priority of Japanese Patent Application No. 2016-072798 filed on Mar. 31, 2016 and Japanese Patent Application No. 2016-186164 filed on Sep. 23, 2016, the entire disclosure of which, including the description, claims, drawings, and abstract, is incorporated herein by reference in its entirety.

BACKGROUND OF THE INVENTION

Field of the Invention

The present invention relates to an electronic apparatus, a notification method, and a computer readable storage medium.

Related Art

Thus far, technology has been disclosed, as in Japanese Unexamined Patent Application, Publication No. 2014-208314, for notifying a user of a movement path that allows the user to consume goal calories based on inputted information relating to a blood sugar value and an exercise amount and notifies the user of advice to change exercise intensity when the pulse rate of the user moving along the movement path deviates from an estimated proper value.

SUMMARY OF THE INVENTION

According to an aspect of the present invention, an electronic apparatus includes a processor, in which the processor executes: acquiring bio-information relating to a subject; successively acquiring activity information relating to activity of the subject; estimating a physical condition of the subject based on the acquired bio-information and the acquired activity information; and performing a notification of first information based on an estimated physical condition of the subject. According to another aspect of the present invention, a notification method includes: firstly acquiring bio-information relating to a subject; secondly acquiring successively activity information relating to activity of the subject; estimating a physical condition of the subject based on the bio-information acquired in the firstly acquiring and the activity information acquired in the secondly acquiring; and performing a notification of information based on an estimated physical condition of the subject in the estimating, to a notification member. According to yet another aspect of the present invention, a non-transitory storage medium is provided which is encoded with a computer-readable program that enables a computer to execute functions as: acquiring bio-information relating to a subject; successively acquiring activity information relating to activity of the subject; estimating a physical condition of the subject based on the acquired bio-information and the acquired activity information; and performing a notification of first information based on an estimated physical condition of the subject.

DETAILED DESCRIPTION OF THE INVENTION

Embodiments of the present invention are explained below with reference to the drawings.

Figure 1:
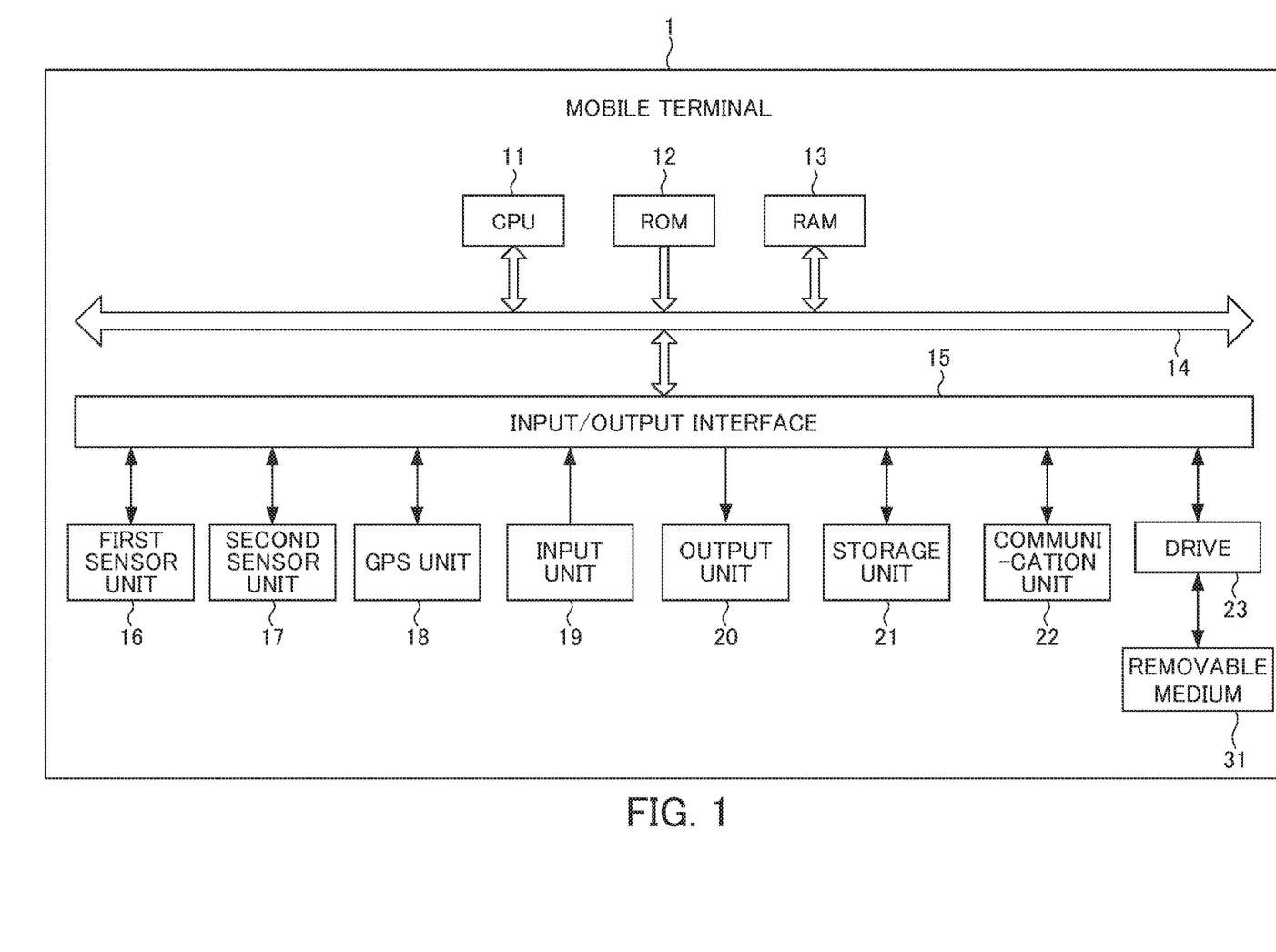
FIG. 1 is a block diagram illustrating a hardware configuration of a mobile terminal 1 according to one embodiment of the present invention.

FIG. 1 is a block diagram showing the hardware configuration of a mobile terminal 1 according to an embodiment of the present invention.

The mobile terminal 1 is configured as a wrist terminal such as a smart watch.

As illustrated in FIG. 1, the mobile terminal 1 includes a CPU (Central Processing Unit) 11, ROM (Read Only Memory) 12, RAM (Random Access Memory) 13, a bus 14, an input/output interface 15, a first sensor 16, a second sensor 17, a GPS (Global Positioning System) unit 18, an input unit 19, an output unit 20, a storage unit 21, a communication unit 22, and a drive 23.

The CPU 11 executes various processing according to programs that are recorded in the ROM 12, or programs that are loaded from the storage unit 21 to the RAM 13.

The RAM 13 also stores data and the like necessary for the CPU 11 to execute the various processing, as appropriate.

The CPU 11, the ROM 12 and the RAM 13 are connected to one another via the bus 14. The input/output interface 15 is also connected to the bus 14. The first sensor unit 16, the second sensor unit 17, the GPS unit 18, the input unit 19, the output unit 20, the storage unit 21, the communication unit 22, and the drive 23 are connected to the input/output interface 15.

The first sensor unit 16 is configured with various kinds of sensors that can acquire bio-information created by sensing a subject's pulse and blood pressure. In the mobile terminal 1 configured by a wrist terminal, the pulse and blood pressure are sensed in real time from an arm of the subject.

The second sensor unit 17 is configured with various kinds of sensors that can acquire environmental information created by sensing the environment around the subject such as humidity, atmospheric temperature, pressure, and weather in real time.

The GPS unit 18 is configured so that positional information can be acquired for which a current position of an own device possessed by the subject is sensed in real time.

The input unit 19 is configured by various buttons and the like, and inputs a variety of information in accordance with instruction operations by the user. The output unit 20 is configured by the display unit, a speaker, and the like, and outputs images and sound.

The storage unit 21 is configured by DRAM (Dynamic Random Access Memory) or the like, and stores data of various images.

The communication unit 22 controls communication with other devices (not shown) via networks including the Internet.

A removable medium 31 composed of a magnetic disk, an optical disk, a magneto-optical disk, semiconductor memory or the like is installed in the drive 23, as appropriate. Programs that are read via the drive 23 from the removable medium 31 are installed in the storage unit 21, as necessary. Similarly to the storage unit 21, the removable medium 31 can also store a variety of data such as the image data stored in the storage unit 21.

The mobile terminal 1 configured as described above has the functions of estimating the consumption amount of water and nutrients which represents physical conditions based on the user's bio-information, the user's activity information, and the environmental information around the user, and estimating a remaining amount of water and nutrients which represents physical conditions based on the estimated consumption amount and the user's bio-information. Then, the mobile terminal 1 has the function of warning as advice when the estimated remaining amount falls below a prescribed value. It should be noted that "bio-information" includes information generated by measuring bodily functions of the subject such as blood pressure, heart rate, and body temperature, for example. In addition, it should be noted that "activity information" includes information created to recognize the user's activities such as walking, running, climbing up a mountain, etc., as activities. It should also be noted that "environmental information" includes information of the environment around the subject such as atmospheric temperature, humidity, and weather. It should also be noted that "physical condition" includes conditions of components which constitute the body such as a water amount and the amount of nutrients in the body of the subject.

Figure 2A:
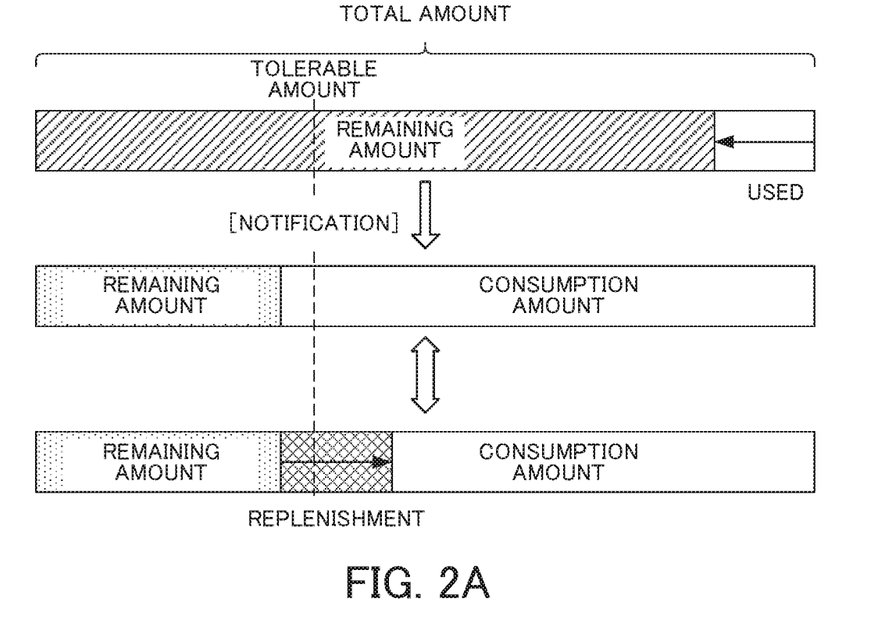
FIG. 2A is a schematic view illustrating a notification pattern.
Figure 2B:
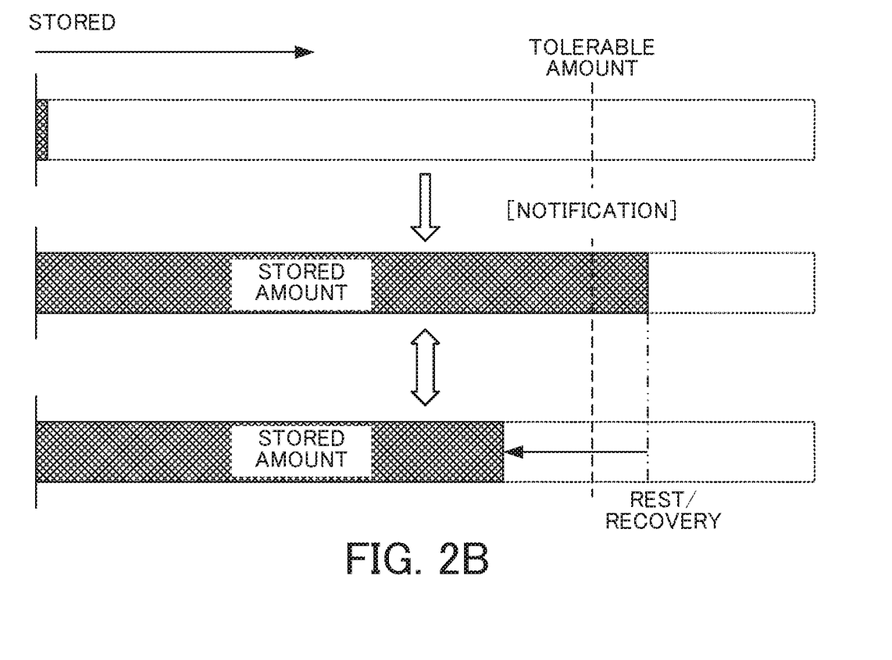
FIG. 2B is a schematic view illustrating a notification pattern.

FIG. 2 is a schematic view illustrating a notification pattern.

In a case of water and nutrients stored in the body, for example, as illustrated in FIG. 2A, the water and nutrients are used (dissipated/consumed) due to activities through sweating, metabolism, exercise, etc.

The mobile terminal 1 monitors by calculating the remaining amount of water and nutrients. In a case in which the consumption progresses due to activities and the remaining amount of the water and the nutrients goes beyond a tolerable amount, the mobile terminal 1 notifies the user of being the timing to replenish and the amount of water and nutrients that should be replenished (notification of the amount of water to be replenished, the amount of food that should be eaten, etc.).

Then, in a case in which the remaining amount increased as a result of the replenishing, the mobile terminal 1 senses the replenishment and monitors by calculating the remaining amount.

In addition, in a case of lactic acid, waste products, etc., stored as a result of fatigue, as illustrated in FIG. 2B, the stored amount increases as fatigue accumulates due to the activities.

The mobile terminal 1 monitors by calculating increased lactic acid and waste product. In a case in which the accumulation progresses due to the activities and the stored amount of lactic acid and waste product goes beyond a tolerable amount, the mobile terminal 1 performs a notification suggesting replenishment, rest, or evacuation, for example.

Then, in a case in which the stored amount decreases as a result of replenishment, rest, or evacuation having been done, the mobile terminal 1 senses the replenishment, rest, or evacuation and monitors by calculating the stored amount.

It should also be noted that the calculation is performed by considering a condition of an individual and the surrounding environment.

In the present embodiment, the remaining amount is calculated by the following formula (1), for example.

$$\text{Remaining Amount} = \text{Total Amount corresponding to Individual} - \text{Consumption Amount corresponding to the Individual under predetermined Environment} \quad (1)$$

"Total Amount corresponding to Individual" is calculated by using individual information of a subject (body height× body weight) and referencing general data of statistics of the total for each individual (body height×body weight), for example (in the present embodiment, individual total amount information, as described later).

"Consumption Amount corresponding to Individual under predetermined Environment" is calculated by using individual information of the subject (body height×body weight) and referencing general data of the consumption amount for the exercise amount of an individual (body height and body weight) under a predetermined environment (for example, under a condition of a predetermined temperature×humidity) (in the present embodiment, environment-individual-consumption-amount information). "Exercise Amount" is calculated from exercise intensity (METs) calculated from the pulse and moving speed.

In addition, using the calculated remaining amount, a dangerous condition is identified based on the difference from an amount permitting life to be normally maintainable (hereinafter, referred to as "tolerable amount"), and a period of entering a dangerous condition is predicted. "Tolerable amount" is calculated by referencing general data of statistics of the tolerable amount for an individual (body height× body weight) (in the present embodiment, individual tolerable amount information as described later).

For example, the mobile terminal 1 is provided with the first sensor unit 16 that serves as a biosensor or an exercise sensor which measures exercise time when exercising or playing sports, measures exercise intensity (heart rate, oxygen intake, METs value, etc.) for every lapse of the exercise time, and the second sensor unit 17 that serves as an environment sensor that detects the surrounding environment such as atmospheric temperature, humidity, and atmospheric pressure.

(1) The mobile terminal 1 calculates and displays consumed calories, fat burning amount, and glycogen (sugar, carbohydrate) combustion amount, etc., during rest, during a halt, and during exercise, according to transition data of the exercise intensity for every lapse of the exercise time from the first sensor unit 16.

Furthermore, the mobile terminal 1 calculates and displays the amount of water consumed during the exercise according to the transition data of the exercise intensity for every lapse of the exercise time from the first sensor unit 16.

(2) The mobile terminal 1 calculates and displays heat quantity released, the sweat amount, or the amount of water lost due to exercise based on the transition data of the exercise intensity for every lapse of the exercise time from the first sensor unit 16 and the transition data of the environment information from the second sensor unit 17.

(3) The mobile terminal 1 calculates and displays a goal and a goal achievement degree moment by moment by setting, in advance, a goal such as a distance of running and an achievement altitude in the case of marathon or mountain climbing, for example.

Furthermore, based on the user's individual information such as sex, age, and body weight, and information relating to physical strength such as an oxygen intake amount and heart rate during a rest and a peak, for example, the mobile terminal 1 sets the total amount of glycogen and water stored in the user's body, successively subtracts the consumed amount of glycogen and water due to exercise from the total amount based on the transition data of exercise intensity for every lapse of the exercise time from the first sensor unit 16, the environment data from the second sensor unit 17, and a replenishment event of nutrients and water during the exercise, and displays the calculated result of the remaining amount of glycogen and water moment by moment. The calculated result can be configured to be displayed in the form of a digital calculation value or a time-series graph, for example.

Furthermore, the tolerable amount can be configured to be set in advance via an individual. However, it may also be configured so that the tolerable amount is reset in real-time according to the change in environment or the change in exercise intensity, for example. More specifically, it can be configured so as to increase the tolerable amount in a case in which an atmospheric temperature increases as the change in environment or exercise becomes intense as the change in exercise intensity. On the other hand, it can be configured so as to decrease the tolerable amount in a case in which the atmospheric temperature decreases as the change in environment or exercise becomes modest as the change in exercise intensity.

Furthermore, the tolerable amount can be configured so as to be reset according to the change in condition of the user's body. For example, it can be configured so as to increase the tolerable amount according to the condition of the user's body such as fever, abdominal pain, and ill health.

Figure 3A:
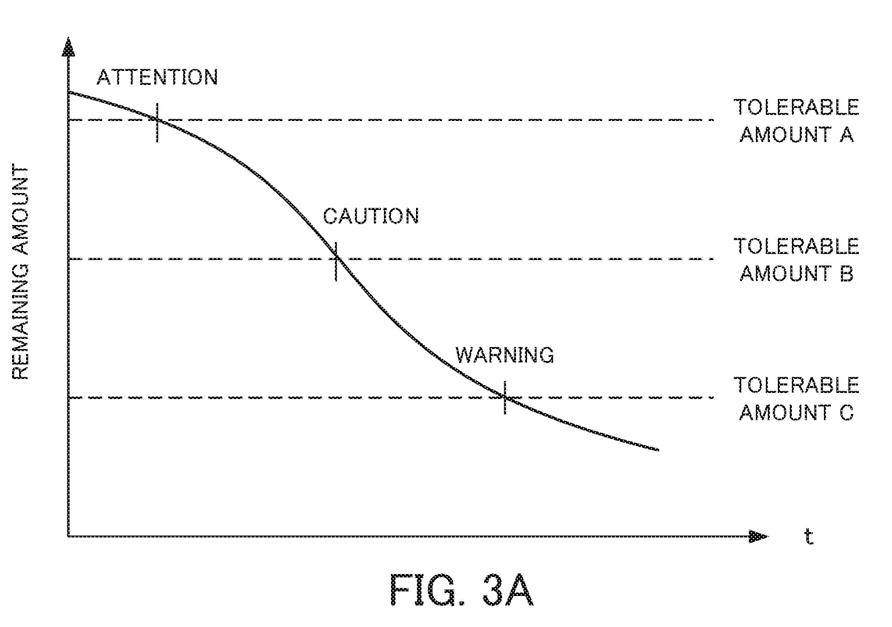
FIG. 3A is a graph illustrating a setting example of a tolerable amount.
Figure 3B:
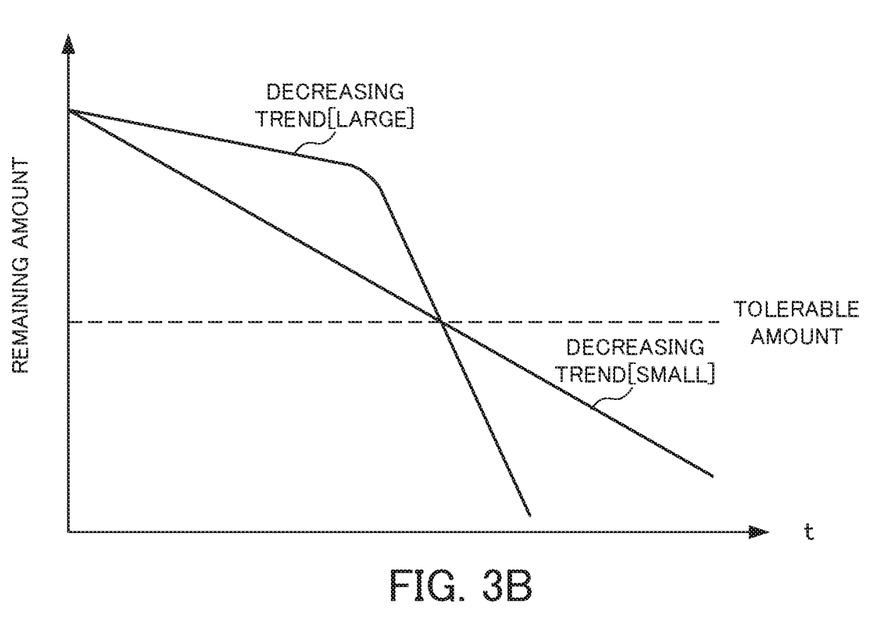
FIG. 3B is a graph illustrating a setting example of a tolerable amount.

FIG. 3 is a graph illustrating a setting example of a tolerable amount.

A plurality of tolerable amounts may be configured to be provided according to the degree of tolerance. In the example of FIG. 3A, the tolerable amounts of the tolerable amount A, the tolerable amount B, and the tolerable amount C, are set according to a level "attention" requiring attention to the remaining amount, a level "caution" requiring caution, and a level "warning" requiring warning, respectively.

In the case of exceeding the tolerable amounts corresponding to each of the levels, the mobile terminal notifies the user of the matter of having exceeding the tolerable amount, the kind of replenishment, time for replenishment, and the degree of emergency, for example, with a message corresponding to each of the levels.

For example, in a case of running for a predetermined period of time, the calories in the user's body are consumed. Therefore, the remaining amount of calories in the user's body exceeds the tolerable amount of "attention". In a case in which the remaining amount of calories in the user's body exceeds the tolerable amount of "attention", the mobile terminal 1 notifies the user of the content of "it would be good to eat a light meal for calorie intake within a few hours", for example. Then, in a case in which the remaining amount of calories in the user's body exceeds the tolerable amount of "caution" by continuing running without the user intaking calories, the mobile terminal 1 changes the replenishment type when exceeding the tolerable amount for "attention", shortens a period until intake, and notifies the user of "please have something sweet within a few minutes".

Then, in a case in which the remaining amount of calories in the user's body exceeds the tolerable amount of "warning" by continuing running without calorie intake, the mobile terminal 1 changes the replenishment type when exceeding the tolerable amount for "caution", further shortens a period until intake, and notifies the user of the content of "please have something high in calories and fast absorbing immediately".

Furthermore, regarding the consumption amount, it is possible to estimate the trends of the consumption based on the environment around the user such as atmospheric temperature and humidity, the contents of the user's exercise (exercise intensity), and the health condition of the user. Furthermore, it may be configured to change the notification contents according to the magnitude of the decreasing trend of the consumption amount.

As illustrated in FIG. 3B, it may be configured so as to change the notification contents when the remaining amount of calories of the user exceeds the tolerable amount between the case of the decreasing trend of the consumption amount being large (decreasing trend (large)) and the case of the decreasing trend of the consumption amount being small (decreasing trend (small)). In the case of the decreasing trend (large), a fast absorbing substance and the matter of emergency being high may be suggested as the notification contents. In the case of the decreasing trend (small), the matter of emergency being low may be suggested as the notification contents.

Furthermore, the decreasing trend of the consumption amount may be determined based on the environment around the user, the content of exercise (exercise intensity), and the user's health condition, for example. For example, in the case of running under intense heat conditions, since water and calories decrease rapidly, it may be determined as the decreasing trend (large). In the case of exceeding the tolerable amount in the state of the decreasing trend (large), a notification of "please have something immediately that is fast absorbing such as sports drink" may be performed, for example.

In the case of walking in cool weather, since water and calories decrease moderately, it is determined as the decreasing trend (small). In the case of exceeding the tolerable amount in the state of the decreasing trend (small), a notification of "please eat a light meal at a convenient timing" may be performed, for example.

Furthermore, it may be configured so as to change the notification contents to the user by combining the decreasing trend of the estimated consumption amount with the level of the tolerable amount that is set.

Figure 4:
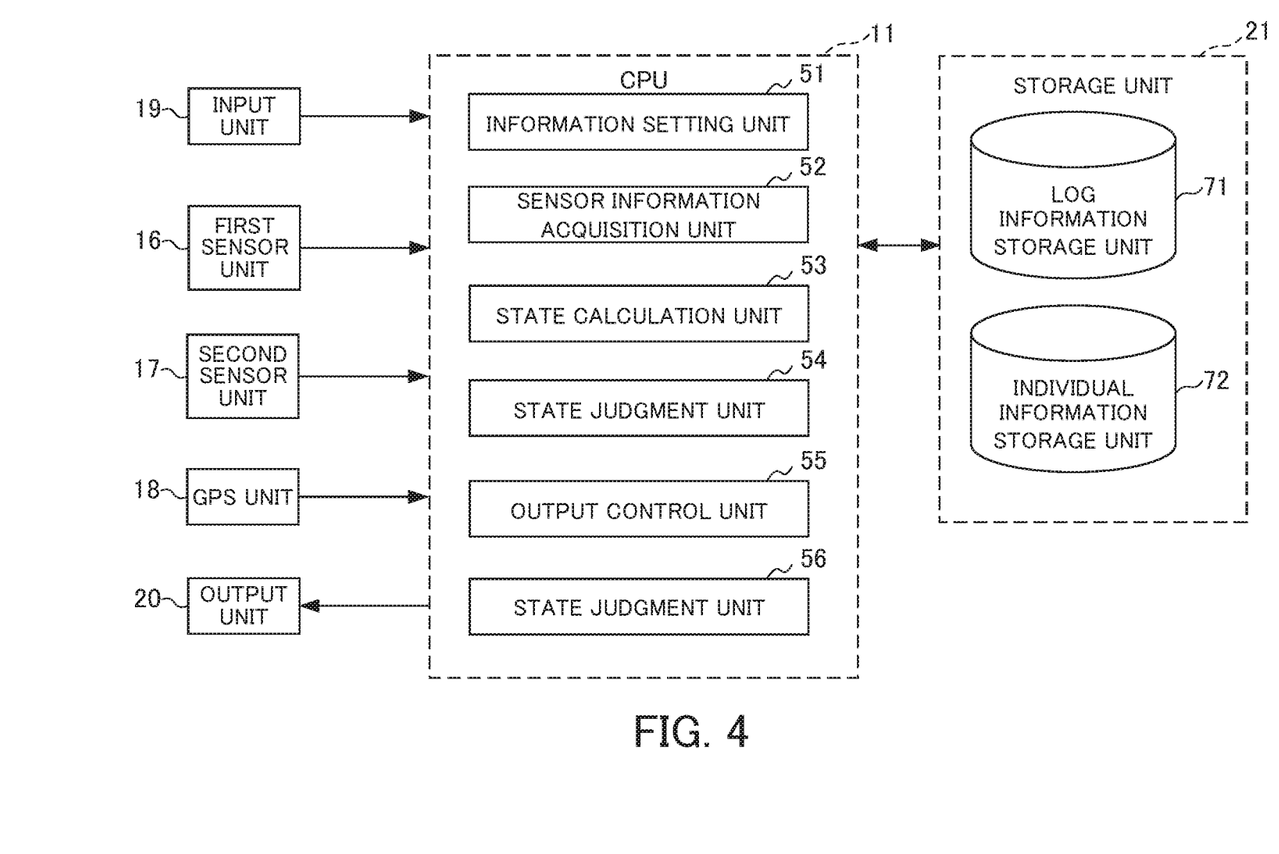
FIG. 4 is a functional block diagram illustrating a functional configuration for executing state management processing among functional configurations of the mobile terminal 1 in FIG. 1.

FIG. 4 is a functional block diagram illustrating a functional configuration for executing state management processing among the functional configurations of the mobile terminal 1 of FIG. 1.

The state management processing refers to a sequence of processing of calculating a consumption amount according to an exercise state from the total amount of water calculated from individual information of a subject and warning when the current amount of water exceeds a tolerable amount while monitoring the current amount of water.

In the case of executing the state management processing, as illustrated in FIG. 4, an information setting unit 51, a sensor information acquisition unit 52, a state calculation unit 53, a state judgment unit 54, an output control unit 55, and a condition judgment unit 56 function in the CPU 11.

In addition, a log information storage unit 71 and an individual information storage unit 72 are provided in a region of the storage unit 21.

In the log information storage unit 71, bio-information acquired from the first sensor unit 16 and environment information acquired from the second sensor unit 17 are stored as log information to be associated with positions and times at the time of acquiring the bio-information and the environment information acquired from the FPS unit 18.

In the individual information storage unit 72, information of the total amount (in the present embodiment, the total amount of water) of each individual (body height×body weight) calculated by statistics (hereinafter, referred to as "individual total amount information"), information of the consumption amount (in the present embodiment, the consumption amount of water) in an exercise amount of each individual (body height×body weight) under a predetermined environment (classified by humidity and atmospheric temperature) (hereinafter, referred to as "environment-individual-consumption-amount information), and the tolerable amount which avoids a dangerous state for each individual (hereinafter, referred to as "individual tolerable amount") are stored as individual information.

The information setting unit 51 sets individual information of the user as a management target (sex, age, height, weight, etc.) and goal information according to an exercise amount such as information relating to a walking course (herein after, referred to as "goal information") by an input operation to the input unit 19 by the user. It should be noted that the information setting unit 51 may be configured so as to set a reference value such as the individual total amount information, the environment-individual-consumption-amount information, and individual tolerable amount, by the user.

The sensor information acquisition unit 52 acquires sensor information outputted from the first sensor unit 16 and the second sensor unit 17 as log information.

For example, the sensor information acquisition unit 52 acquires a pulse from the first sensor unit 16, bio-information such as blood pressure, and the time when the bio-information was acquired, and stores them as log information in the log information storage unit 71.

In addition, the sensor information acquisition unit 52 acquires environment information such as humidity, atmospheric temperature, atmospheric pressure, weather, etc., from the second sensor unit 17, and the position where the environment information was acquired and the time when the environment information was acquired, and stores them as log information in the log information storage unit 71.

The state calculation unit 53 calculates the consumption amount, the remaining amount, and the tolerable amount which are indices for changes in the user's physical condition.

For example, the state calculation unit 53 calculates the consumption amount according to the following procedure.

Initially, the state calculation unit 53 calculates an exercise amount based on the bio-information such as a pulse of the user and a moving distance.

Then, the state calculation unit 53 refers to the environment-individual-consumption-amount information stored in the individual information storage unit 72 based on the individual information, the environment information, and the exercise amount thus calculated, and calculates the consumption amount of the user under a relevant environment.

Furthermore, the state calculation unit 53 calculates a remaining amount according to the following procedure.

Initially, the state calculation unit 53 refers to individual total amount information stored in the individual information storage unit 72 based on the individual information and calculates a relevant total amount.

Then, the state calculation unit 53 calculates a remaining amount by subtracting the consumption amount thus calculated from the calculated total amount.

Then, in a case in which there is replenishment such as drinking water or eating a meal, the state calculation unit 53 adds the replenished portion to the remaining amount.

Furthermore, the state calculation unit 53 calculates a tolerable amount according to the following procedure.

For example, the state calculation unit 53 calculates the tolerable amount based on the individual information.

In a case in which there was a change in environment or exercise intensity, the state calculation unit 53 considers the environment and the exercise intensity and re-calculates the tolerable amount. When the atmospheric temperature increases as a change in environment or exercise becomes intense as a change in exercise intensity, the state calculation unit 53 increases the tolerable amount. On the other hand, when the atmospheric temperature decreases as a change in environment or exercise becomes modest as a change in exercise intensity, the state calculation unit 53 decreases the tolerable amount.

Furthermore, the tolerable amount can provide and set a level according to the user's setting and the like.

For example, as illustrated in FIG. 3A, it is possible to set the tolerable amount of (attention), the tolerable amount of (caution), and the tolerable amount of (warning).

In such a case, with the calculated tolerable amount as the tolerable amount of (warning), the state calculation unit 53 may add a predetermined ratio (or biases by a predetermined ratio) to a slight direction (plus direction) to establish the tolerable amount of (caution), and further add a predetermined ratio to establish the tolerable amount of (attention), or, with the calculated tolerable amount as the tolerable amount of (caution), may add a predetermined value to a slight direction (plus direction) to establish the tolerable amount of (attention) and add a predetermined value to a severe direction (minus direction) to establish the tolerable amount of (warning).

The state judgment unit 54 judges an environment around a subject and a state of the subject.

The state judgment unit 54 judges the environment around the subject and a change in environment from the environment information such as the latest and current humidity, atmospheric temperature, and weather among the log information stored in the long information storage unit 71. Furthermore, the state judgment unit 54 judges exercise intensity based on the exercise amount and the like calculated by the state calculation unit 53.

Furthermore, the state judgment unit 54 judges whether the current remaining amount exceeds the tolerable amount. The state judgment unit 54 refers to the individual tolerable amount information stored in the individual information storage unit 72 based on individual information and calculates the tolerable amount for the individual.

The state judgment unit 54 compares the calculated tolerable amount with the remaining amount calculated by the state calculation unit 53 and judges whether the remaining amount exceeds the tolerable amount.

In a case in which it is judged that the remaining amount exceeds the tolerable amount, it enters a state in which the remaining amount is insufficient as an amount necessary for supporting the user's life.

The output control unit 55 controls the output unit 20 to perform display.

For example, in a case in which the state judgment unit 54 judges that the remaining amount exceeds the tolerable amount, the output control unit 55 controls the output unit 20 to notify that the remaining amount is insufficient as the amount necessary for supporting the user's life and replenishment or a rest is required.

In the output unit 20, output is performed such as displaying a message, performing a voice announcement, and urging the user for caution by means of light, sound, or vibration, for example, and thus a call for attention related to replenishment timing and replenishment amount is brought to the user.

The condition judgment unit 56 judges whether replenishment was performed or rest was taken based on bio-information from the first sensor unit 16 or an input operation to the input unit 19 by the user. In addition, the condition judgment unit 56 can judge the contents of the replenishment or the rest such as the replenishment amount and a rest time period, in addition to whether the replenishing was performed or the rest was taken.

Figure 5:
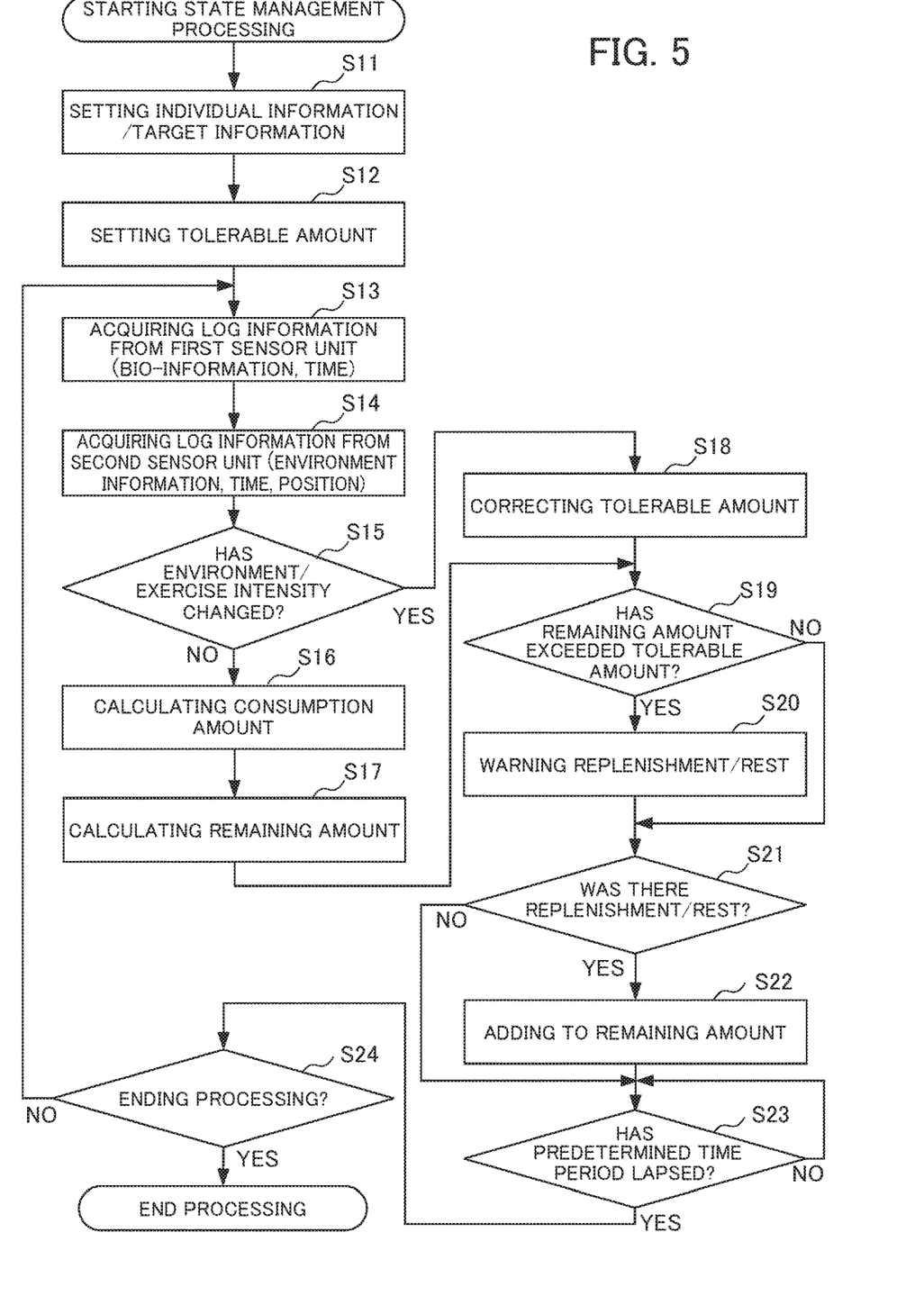
FIG. 5 is a flowchart illustrating a flow of state management processing executed by the mobile terminal 1 in FIG. 1 having the functional configuration of FIG. 4.

FIG. 5 is a flowchart illustrating a flow of state management processing executed by the mobile terminal 1 in FIG. 1 having the functional configuration of FIG. 4.

The state management processing is started by an operation of starting the state management processing to the input unit 19 by the user.

In Step S11, the information setting unit 51 sets individual information of a management target (sex, age, height, weight, etc.) and goal information such as a moving course and an exercise goal, by input operation to the input unit 19 by the user.

In Step S12, the state calculation unit 53 calculates and sets the tolerable amount based on individual information of a management target (sex, age, height, weight, etc.).

In Step S13, the sensor information acquisition unit 52 successively acquires bio-information such as a pulse and blood pressure from the first sensor 16 and the time when the bio-information was acquired, and stores them as log information in the log information storage unit 71.

In Step S14, the sensor information acquisition unit 52 successively acquires environment information such as humidity and atmospheric temperature from the second sensor unit 17 and the position where the environment information was acquired and the time when the environment information was acquired from the GPS unit 18, and stores them as log information in the log information storage unit 71.

In Step S15, the state judgment unit 54 judges whether environment/exercise intensity changed. The state judgment unit 54 judges a change in environment based on environment information such as latest and current humidity, atmospheric temperature, and weather among the log information stored in the log information storage unit 71. Furthermore, the state judgment unit 54 judges a change in exercise intensity based on the bio-information among the log information stored in the log information storage unit 71, for example.

In a case in which the environment/exercise intensity has not changed, it is judged as NO in Step S15, and the processing advances to Step S17.

In a case in which the environment/exercise intensity has changed, it is judged as YES in Step S15, and the processing advances to Step S16.

In Step S16, the state calculation unit 53 corrects the tolerable amount according to the changed environment/exercise intensity. The state calculation unit 53 considers environment and exercise intensity and re-calculates the tolerable amount for correction. When the atmospheric temperature increases as a change in environment or exercise becomes intense as a change in exercise intensity, the state calculation unit 53 increases the tolerable amount. On the other hand, when the atmospheric temperature decreases as a change in environment or exercise becomes modest as a change in exercise intensity, the state calculation unit 53 decreases the tolerable amount.

In Step S17, the state calculation unit 53 calculates a consumption amount (in the present embodiment, the consumption amount of water) based on the individual information, the bio-information, and the environment information thus acquired.

For example, the state calculation unit 53 calculates an exercise amount based on the bio-information and a moving distance, and refers to environment-individual-consumption-amount information stored in the individual information storage unit 72 based on the individual information, the environment information, and the exercise amount thus calculated so as to calculate the consumption amount for the individual under a relevant environment.

In addition, when the environment/exercise intensity has changed, the state calculation unit 53 does not consider the current environment or the current exercise intensity, but considers a change portion so as to calculate an anticipated consumption amount based on the change.

In Step S18, the state calculation unit 53 calculates the remaining amount based on the individual information and the consumption amount thus calculated (in the present embodiment, the remaining amount of water).

For example, the state calculation unit 53 refers to the individual total amount information stored in the individual information storage unit 72 based on the individual information so as to calculate a relevant total amount, and subtracts the calculated consumption amount from the calculated total amount so as to calculate the remaining amount.

In Step S19, the state judgment unit 54 judges whether the remaining amount exceeds the tolerable amount. For example, the state judgment unit 54 refers to the individual tolerable amount information stored in the individual information storage unit 72 based on the individual information so as to calculate an individual tolerable amount, and compares the calculated tolerable amount with the remaining amount calculated by the state calculation unit 53 so as to judge whether the remaining amount exceeds the tolerable amount.

In a case in which the remaining amount does not exceed the tolerable amount, it is judged as NO in Step S19 and the processing advances to Step S21.

In a case in which the remaining amount exceeds the tolerable amount, it is judged as YES in Step S19 and the processing advances to Step S20.

In Step S20, since the remaining amount exceeds the tolerable amount, water is insufficient for the individual. Therefore, the output control unit 55 controls the output unit 20 so as to output a warning to urge the user to receive replenishment or take a rest. The output unit 20 outputs an alarm or a warning message, for example, to call for attention of the user.

In Step S21, the condition judgment unit 56 judges whether the replenishment was received or the rest was taken. For example, whether the rest was taken is judged based on an input operation by the user to the input unit 19 or bio-information, and whether the replenishment was received is judged based on an input of a replenishment target or a replenished amount by the user.

In a case in which replenishment was not received or a rest was not taken, it is judged as NO in Step S21, and the processing advances to Step S23.

In a case in which replenishment was received and a rest was taken, it is judged as YES in Step S21, and the processing advances to Step S22.

In Step S22, the state calculation unit 53 adds an amount recovered by a replenishment amount or the rest to the remaining amount. The state calculation unit 53 adds a replenishment amount to the remaining amount.

In Step S23, the CPU 11 judges whether a predetermined time period has lapsed.

In a case in which a predetermined time period has not lapsed, it is judged as NO in Step S23, and the processing enters a waiting status.

In a case in which a predetermined time period has lapsed, it is judged as YES in Step S23, and the processing advances to Step S24.

In Step S24, the CPU 11 judges whether there was an operation to end the processing by the user on the input unit 19.

In a case in which there is no operation to end the processing, it is judged as NO in Step S24, and the processing returns to Step S13.

In a case in which there is an operation to end the processing, it is judged as YES in Step S24, and the state management processing ends.

According to the mobile terminal 1, it is configured to calculate a retaining total amount of water based on the individual information of the subject to estimate a consumption amount based on exercise and the environment around the user. However, it may also be configured by calorie, energy, etc., so that a consumption amount can be recognized based on individual information and exercise amount.

Furthermore, according to the mobile terminal 1, it may be configured to provide advice for achieving a goal using goal information. In such a case, it may be configured to provide advice relating to replenishment and a rest for achieving the goal, and perform maintenance management of a remaining amount in order to achieve the goal.

Furthermore, according to the mobile terminal 1, notification and the like can be performed by performing prediction for a consumption amount and the like in the future based on a change in the consumption amount in a latest predetermined time period. The notification is performed in relation to the tolerable amount in the abovementioned embodiment. However, the present invention is not limited thereto, and such notification can be performed by displaying a current status or a change on a graph, for example.

Modified Embodiment

Although the embodiments are exemplified using the amount of water in the abovementioned embodiments, consumed calories, fat and carbohydrate burning amounts, perspired amount, etc., can be calculated as shown below, for example.

Example of Calculating Consumed Calories During Life Activity

Consumed Calories [kcal]=(Body Activity Level 1.0)×Basal Metabolism Reference Value for Each Individual classified by Sex and Age [kcal/kg/minute]×Weight [kg]×Active Time [Minute]

Example of Calculating Consumed Calories During Mountain Climbing

Consumed Calories during Mountain Climbing [kcal]=4.99×(10^(−6)×(Load of Mountain Climbing)^2+0.0009×(Load of Mountain Climbing)+0.73)×Exercise Time [Minutes]

In addition,

Load of Mountain Climbing [workload][kg·m/Minute]=[Weight+Load][kg]×Moving Amount in Vertical Direction/Moving Time Period][m/Minute]

Example of Calculating Consumed Calories During Walking

Consumed Calories during Walking [kcal]=0.0283÷ (1−(Exercise Speed [m/Minute]/Reference Speed 242))^2×Exercise Time [Minute]×Weight [kg]×Corrected Value for Each Individual classified by Sex and Age Example of Calculating Consumed Calories During Jogging/Running Consumed Calories during Jogging/Running [kcal] =0.00492×(0.2×Speed [m/Minute]+3.5)×Exercise Time [Minute]×Weight [kg]×Corrected Value for Each Individual classified by Sex and Age Example of Calculating Consumed Calories During Other Exercise Consumed Calories during other Exercise [kcal] =Basal Metabolism Reference Value for Each Individual classified by Sex and Age [kcal/kg/min]×[Exercise Intensity [RMR]+1.2]×Exercise Time [Minute]×Weight [kg], or =1.05×Exercise Intensity [METs]×Exercise Time [Minute]/60× Weight [kg]×Corrected Value for Each Individual classified by Sex and Age Example of Calculating Consumed Calories Based on Heart Rate Consumed Calories based on Heart Rate [kcal] =Oxygen Intake Amount [ml/kg/Minute]× 0.00492 [kcal/ml]×Exercise Time [Minute]× Weight [kg]×Corrected Value for Each Individual classified by Sex and Age In addition, Oxygen Intake Amount [ml/kg/Minute]=[Unskilled Person: 0.28,Skilled Person: 0.325]×Heart Rate [Heart Rate/Minute]−18

Example of Calculating Fat Burning Amount

Fat Burning Amount [g]=Consumed Calories [kcal]× Fat Burning Rate [%]/7.2 [kcal/g]

In addition,

Fat Burning Rate [%]=51% to 50%←Exercise Intensity [Maximum Oxygen Intake Rate: % VO2 max]=30% to 40%,Fat Burning Rate [%]=47% to 42%←Exercise Intensity [Maximum Oxygen
Intake Rate: % VO2 max]=50% to 60%,Fat
Burning Rate [%]=up to 33%←Exercise Intensity [Maximum Oxygen Intake Rate: % VO2
max]=no less than 70%

<Burning Amount of Carbohydrate>

Carbohydrate Burning Amount [g]=Consumed Calories [kcal]×Carbohydrate Burning Rate [%]/7.2
[kcal/g]

In addition,

Carbohydrate Burning Rate [%]=100%−Fat Burning
Rate,Fat Burning Rate [%]=51% to 50%←Exercise Intensity [Maximum Oxygen Intake Rate:
% VO2 max]=30% to 40%,Fat Burning Rate
[%]=47% to 42%←Exercise Intensity [Maximum Oxygen Intake Rate: % VO2 max]=50%
to 60%,Fat Burning Rate [%]=up to
33%←Exercise Intensity [Maximum Oxygen
Intake Rate: % VO2 max]=no less than 70%

<Calculating Exercise Intensity [Maximum Oxygen Intake Rate: % VO2 max] from Heart Rate>

Exercise Intensity [Maximum Oxygen Intake Rate:
% VO2 max]=Oxygen Intake Amount [VO2]
[ml/[kg Minute]/Maximum Oxygen Intake
Amount [ml/[kg Minute]×100

In addition,

Oxygen Intake Amount [ml/kg/Minute]=[Unskilled
Person: 0.28,Skilled Person: 0.325]×Heart Rate
[Heart Rate/Minute]−18

Alternatively,

Exercise Intensity [Maximum Oxygen Intake Rate:
% VO2 max]=% HRmax=[Heart Rate [Heart
Rate/Minute]−Heart Rate during Rest]/[Maximum Heart Rate/Heart Rate during Rest]

<Calculating Corresponding Exercise Intensity (Maximum Oxygen Intake Rate: % VO2 max) from Exercise Intensity (METs or RMR)>

METs=3.0 to 3.8→% VO2 max=40%,METs=4.6→%
VO2 max=50%,METs=5.5→% VO2 max=60%,
METs=6.3 to 7.2→% VO2 max=70%,
METs=8.0→% VO2 max=80%, <Calculating Perspiration Amount during Mountain Climbing [Case of Humidity being 40% to 60%]>

Perspiration Amount [ml/hour]=0.15×Atmospheric
Temperature $T$ [° C.]$^2$+0.55×Humidity RH
[%]+1.85×Humidity RH [%],provided a case of
Weight+Load=75 kg,altitude arrival
speed=250m/hour,in a case of ={−0.002×Atmospheric Temperature $T$ [° C.]$^2$+0.0073×Humidity RH [%]×Atmospheric Temperature $T$ [° C.]+
0.0247×Humidity RH [%]×[Weight+Load]W
[kg]×(Moving Speed in Vertical Direction)[m/
hour]/250), or in a case of ≈2 [ml]×Weight
[kg]×Exercise Time [hour]

Furthermore, it may also be configured so as to set an individual profile beforehand when performing a calculation.

For example, the individual profile is set, for example, by calculating a physical strength level such as a maximum oxygen intake amount and a maximum heart rate classified by age based on, for example, age, sex, body height, body weight, load, basal metabolism reference value for each individual classified by age and sex, corrected value for each individual classified by age and sex, the ordinary body activity levels 1 to 3, Cooper Test, simple physical performance test, Uth-Sorensen-Overgaard-Pedersen estimate (maximum heart rate, heart rate during rest, etc.), etc.

The mobile terminal 1 is configured to estimate not only an exercise amount (number of steps taken, running distances), an exercise performance, a consumed calorie amount, a fat burning amount, etc., as with conventional pedometers or fitness trackers, but also a consumed amount of glycogen (or sugar and carbohydrate) during exercise, a consumed amount of water (perspiration amount), etc., so that the mobile terminal 1 warns the user or notifies the user by prediction before exposing the user's body to danger even during strenuous sports such as mountain climbing and marathon running or activities which unexpectedly consume water, nutrients, and physical strength.

With such a configuration, the user can continue his/her exercise in a safer manner while maintaining his/her pace and conserving physical strength.

The mobile terminal 1 configured as above includes the sensor information acquisition unit 52, the state calculation unit 53, and the output control unit 55.

The sensor information acquisition unit 52 successively acquires bio-information relating to a subject.

The sensor information acquisition unit 52 acquires activity information relating to the subject's activities.

The state calculation unit 53 estimates the subject's physical condition based on the bio-information acquired by the sensor information acquisition unit 52 and the activity information acquired by the sensor information acquisition unit 52.

The output control unit 55 controls the output unit 20 to perform a notification of information based on the subject's physical condition estimated by the state calculation unit 53.

With such a configuration, the mobile terminal 1 notifies the user of information which urges the user for replenishment of nutrients and water according to a change in the user's physical condition.

The information thus notified of includes information that urges replenishment to the user based on an estimated result by the state calculation unit 53.

With such a configuration, the mobile terminal 1 can notify the user of the information that urges replenishment to the user according to a change in the user's physical condition.

The information thus notified of includes information relating to replenishment type that should be replenished or replenishment timing based on the estimated result by the state calculation unit 53.

With such a configuration, the mobile terminal 1 can perform the notification of the information relating to the replenishment type that should be replenished or replenishment timing according to a change in the user's physical condition.

The sensor information acquisition unit 52 acquires bio-information relating to a body of the subject in real-time and acquires activity information relating to the subject's activities in real-time.

The state calculation unit 53 estimates a change in the subject's physical condition based on the bio-information and the activity information acquired by the sensor information acquisition unit 52.

With such a configuration, the mobile terminal 1 can perform a notification according to the change in the user's physical condition based on the current situation.

The mobile terminal 1 further includes the state judgment unit 54 which compares the estimated result with a predetermined reference relating to the subject's physical condition.

The output control unit 55 controls the output unit 20 to perform a notification based on a comparison result by the state judgment unit 54.

With such a configuration, the mobile terminal 1 can perform a notification to prevent the subject's physical condition from deteriorating in advance in a simple manner.

The mobile terminal 1 further includes the information setting unit 51 which sets a predetermined reference relating to the subject's physical condition based on the bio-information of the subject.

With such a configuration, the mobile terminal 1 can perform a notification to prevent the subject's physical condition from deteriorating in advance in a simple manner based on the reference which was set.

The sensor information acquisition unit 52 acquires environment information relating to the environment around the subject.

The state calculation unit 53 estimates the subject's physical condition based on the environment information, the bio-information, and the activity information acquired by the sensor information acquisition unit 52.

With such a configuration, since the mobile terminal 1 estimates the subject's physical condition based on the environment information, the bio-information, and the activity information, the mobile terminal 1 can estimate information according to a change in the subject's physical condition with higher precision.

The sensor information acquisition unit 52 acquires an activity schedule of the subject.

The output control unit 55 controls the output unit 20 to perform a notification of information based on the physical condition of the subject by the state calculation unit 53 and the activity schedule of the subject acquired by the sensor information acquisition unit 52.

With such a configuration, the mobile terminal 1 can perform a notification according to a change in the user's physical condition based on the activity schedule.

The information includes information relating to replenishment timing or amount of water or nutrients by the subject.

With such a configuration, the mobile terminal 1 can perform a notification of information relating to replenishment timing or amount of water or nutrients by the subject.

The physical condition includes conditions of the amount of water in the subject' body and the amount of nutrients in the subject's body.

With such a configuration, the mobile terminal 1 can perform a notification of information due to the conditions of the amount of water in the subject' body and the amount of nutrients in the subject's body.

When the subject replenishes water or nutrients, the state calculation unit 53 estimates the subject's physical condition based on the amount of water or the amount of nutrients replenished.

With such a configuration, the mobile terminal 1 can perform a notification of information according to a change in the user's physical condition by considering the recovery of the physical condition of the user.

It should be noted that the present invention is not to be limited to the aforementioned embodiments, and that modifications, improvements, etc. within a scope that can achieve the objects of the present invention are also included in the present invention.

Although the abovementioned embodiments are configured to adopt the method of estimating the stored, remaining, or consumed glycogen amount or water amount based on exercise intensity and exercise time (for example, heart rate and exercise intensity) which are important for marathon running or mountain climbing, environment data (for example, atmospheric temperature, humidity), and individual attributes (for example, sex, age, body weight, and physical strength), another method may be adopted. For example, a rougher amount of necessary nutrients or water may be used for estimation.

Furthermore, it may be configured to adopt another index such as heart rate, body temperature (inside underwear or at a body surface), humidity, the degree of oxygen saturation, the amount of water consumed, the number of urination times, etc., and it may also be configured so as to select and add indices.

Furthermore, although it is configured so that the tolerable amount is calculated in advance based on the user's physical condition in the abovementioned embodiment, it may be configured to change/set the tolerable amount in real-time by considering environment information that is successively acquired. For example, when humidity or atmospheric temperature is high, it may be configured to set a standard tolerable amount to be high, or when humidity or atmospheric temperature is in an optimal state, it may be configured to set the standard tolerable amount to be relatively low.

In addition, it may also be configured to change/set the tolerable amount in real-time by considering current bio-information. For example, in a case in which it is judged that the user is ill based on the bio-information, it may set the standard tolerable amount to be relatively high. Furthermore, in a case in which humidity or atmospheric temperature is in an optimal condition or the user is in good physical condition based on the bio-information, it may also be configured to set the standard tolerable amount to be relatively low.

Furthermore, it may also be configured to change the degree of change in a consumption amount in real-time by considering the current environment information or bio-information. For example, in a case in which humidity or atmospheric temperature is high or the user is in good physical condition and the metabolism increases based on the bio-information, it may be configured to increase the degree of the consumption amount.

Furthermore, although a message is displayed on the output unit 20 and a notification is performed with sound, light, vibration, and the like in the abovementioned embodiments, it may be configured to advise the user by a sound at predetermined timing or call for attention of the user by displaying a transition of the consumption amount and the tolerable amount on a graph.

Furthermore, in the abovementioned embodiments, it may be configured to perform a notification at the timing at which replenishment is required, perform a notification of a prediction before the timing of replenishment, or perform a notification in a case beyond a limit after the timing of replenishment.

Furthermore, in the abovementioned embodiments, the contents of the notification include a consumption amount, replenishment amount, replenishment timing, and a content of replenishment.

The contents of the abovementioned notification may be configured to be notified singularly or in any combination.

Furthermore, in the abovementioned embodiments, by considering multiple items such as the amount of water, calories, etc. in order to handle the user's physical condition, it can be configured to perform a notification or allow the user to recognize the current condition by displaying a gauge for the physical condition when exceeding the tolerable amount of each item.

Furthermore, in the abovementioned embodiment, it may be configured to correspond to various kinds of things including water such as sports drinks, solid food, and semisolid food such as jelly, as an object which is urged to replenish to the user.

Furthermore, in the abovementioned embodiments, it may be configured to perform a notification with a content which can be intuitively understood or with a specific time by considering an emergency level of replenishment such as "now", "within . . . minutes", and "after . . . minutes". Furthermore, it may be configured to display a message by highlighting it, outputting it using a sound, increasing the volume of the sound, using a vibration, or using the combination thereof, according to the emergency level.

Furthermore, although it is configured to perform a notification of a kind of replenishment, content, and amount according to the abovementioned embodiments, it may also be configured to perform a notification of the temperature of the replenishment when replenishing. In such a case, it may be configured to determine the temperature during replenishment based on an environment around the subject, a condition of the subject, and kind of replenishment.

For example, in a case in which the user exercises under the blazing sun, it may be configured to perform a notification of urging the user not to drink extremely cold sports drink but to drink a sports drink with at air temperature by considering the sudden drop in temperature of the user's body. Furthermore, in a case in which the body temperature is relatively high when comparing with an outside air temperature, it may be configured to perform a notification of urging the user to replenish in a step-wise manner such as drinking a cold drink first and then a drink having a higher temperature so as to lower the body temperature but not to lower the body temperature too much.

Furthermore, it may be configured so that the abovementioned embodiments are configured with the mobile terminal 1 as a wearable terminal, another mobile terminal such as Smartphone, and a server, etc., communication is performed at any time by means of near field communication, etc., between the mobile terminal 1 and another mobile terminal, information sensed by the mobile terminal 1 is uploaded to the server via another mobile terminal, management and the like is performed at the server, and display is performed at the mobile terminal 1 only.

In the aforementioned embodiments, explanations are provided with the example of the mobile terminal 1 to which the present invention is applied being a smart watch; however, the present invention is not limited thereto in particular.

For example, the present invention can be applied to any electronic device in general having a state management processing function.

More specifically, for example, the present invention can be applied to a laptop personal computer, a printer, a television receiver, a video camera, a portable navigation device, a cell phone device, a digital camera, a smartphone, a portable gaming device, and the like.

The processing sequence described above can be executed by hardware, and can also be executed by software.

In other words, the hardware configurations of FIG. 4 are merely illustrative examples, and the present invention is not particularly limited thereto. More specifically, the types of functional blocks employed to realize the above-described functions are not particularly limited to the examples shown in FIG. 4, so long as the mobile terminal 1 can be provided with the functions enabling the aforementioned processing sequence to be executed in its entirety.

A single functional block may be configured by a single piece of hardware, a single installation of software, or a combination thereof.

The functional configurations of the present embodiment are realized by a processor executing arithmetic processing, and processors that can be used for the present embodiment include a unit configured by a single unit of a variety of single processing devices such as a single processor, multi-processor, multi-core processor, etc., and a unit in which the variety of processing devices are combined with a processing circuit such as ASIC (Application Specific Integrated Circuit) or FPGA (Field-Programmable Gate Array).

In a case in which the processing sequence is executed by software, the program configuring the software is installed from a network or a storage medium into a computer or the like.

The computer may be a computer embedded in dedicated hardware. Alternatively, the computer may be a computer capable of executing various functions by installing various programs, e.g., a general-purpose personal computer.

The storage medium containing such a program can not only be constituted by the removable medium 31 of FIG. 1 distributed separately from the device main body for supplying the program to a user, but also can be constituted by a storage medium or the like supplied to the user in a state incorporated in the device main body in advance. The removable medium 31 is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, ROM 12 of FIG. 1 in which the program is recorded or a hard disk, etc. included in the storage unit 21 of FIG. 1.

It should be noted that, in the present specification, the steps defining the program recorded in the storage medium include not only the processing executed in a time series following this order, but also processing executed in parallel or individually, which is not necessarily executed in a time series.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

What is claimed is:

1. An electronic apparatus comprising:
a processor configured to:
  at a first time, set a first value of a tolerable amount of the physical condition of the subject; and
  after the first time:
    control one or more sensors to receive signals output from the sensors and, based on the received signals, to:

acquire a plurality of values of bio-information relating to bodily functions of a subject over time;
acquire a plurality of values of activity information relating to activity of the subject over time; and
acquire a plurality of values of environmental information relating to an environment around the subject over time;
estimate a remaining amount of a physical condition of the subject based on the plurality of values of bio-information the plurality of values of activity information, and the plurality of values of environmental information;
at a second time after the first time, determine whether there is a change in an intensity of one or more of the plurality of values of the bio-information, the plurality of values of the activity information, and the plurality of values of the environmental information over time;
in response to determining that there is no change in the intensity of the plurality of values of the bio-information, the plurality of values of the activity information, and the plurality of values of the environmental information over time:
perform a first comparison of the remaining amount of the physical condition to the first value of the tolerable amount of the physical condition; and
determine whether to perform a notification of information based on a result of the first comparison; and
in response to determining that there is a change in the intensity of one or more of the plurality of values of the bio-information, the plurality of values of the activity information, and the plurality of values of the environmental information over time:
correct the tolerable amount of the physical condition from the first value to a second value;
perform a second comparison of the remaining amount of the physical condition to the second value of the tolerable amount of the physical condition; and
determine whether to perform the notification of the information based on a result of the second comparison.

2. The electronic apparatus according to claim 1, wherein the information to be notified includes information that urges the subject to replenish based on the remaining amount of the physical condition estimated.

3. The electronic apparatus according to claim 1, wherein the information to be notified includes information on a kind of replenishment, an amount of replenishment, or replenishing timing of the replenishment based on the remaining amount of the physical condition estimated.

4. The electronic apparatus according to claim 1, wherein the processor is configured to:
acquire an activity schedule of the subject; and
determine whether to perform the notification of the information based on the activity schedule acquired and on the result of the first comparison or the second comparison.

5. The electronic apparatus according to claim 1, wherein the processor is configured to estimate a decreasing trend of the remaining amount of the physical condition.

6. The electronic apparatus according to claim 5, wherein the processor is configured to:
in response to determining to perform the notification of the information based on the result of the first comparison or the result of the second comparison, select one of a plurality of contents of the information to be notified based on the amount of the decreasing trend of the remaining amount of the physical condition estimated.

7. The electronic apparatus according to claim 1, wherein the physical condition comprises an amount of water or an amount of nutrients in a body of the subject.

8. The electronic apparatus according to claim 5, wherein the processor is configured to, after performance of the notification of the information based on the result of the first comparison or the result of the second comparison:
determine a replenishment amount of the physical condition; and
re-estimate the remaining amount of the physical condition of the subject based on the replenishment amount of the physical condition.

9. The electronic apparatus according to claim 1, wherein the processor is configured to control an output device to perform the notification of the information.

10. The electronic apparatus according to claim 9, further comprising the output device, wherein the output device comprises a display and a speaker.

11. The electronic apparatus according to claim 1, further comprising a transmission member, wherein the processor is configured to control the transmission member to send, to an external output device, an instruction to perform the notification of the information.

12. A notification method comprising:
at a first time, setting a first value of a tolerable amount of the physical condition of the subject; and
after the first time:
controlling one or more sensors to receive signals output from the sensors and, based on the received signals, to:
acquire a plurality of values of bio-information relating to bodily functions of a subject over time;
acquire a plurality of values of activity information relating to activity of the subject over time; and
acquire a plurality of values of environmental information relating to an environment around the subject over time;
estimating a remaining amount of a physical condition of the subject based on the plurality of values of bio-information, the plurality of values of activity information, and the plurality of values of environmental information;
at a second time after the first time, determining whether there is a change in an intensity of one or more of the plurality of values of the bio-information, the plurality of values of the activity information, and the plurality of values of the environmental information over time;
in response to determining that there is no change in the intensity of the plurality of values of the bio-information, the plurality of values of the activity information and the plurality of values of the environmental information over time:
  performing a first comparison of the remaining amount of the physical condition to the first value of the tolerable amount of the physical condition; and
  determining whether to perform a notification of information based on a result of the first comparison; and
in response to determining that there is a change in the intensity of one or more of the plurality of values of the bio-information, the plurality of values of the activity information, and the plurality of values of the environmental information over time:
  correcting the tolerable amount of the physical condition from the first value to a second value;
  performing a second comparison of the remaining amount of the physical condition to the second value of the tolerable amount of the physical condition; and
  determining whether to perform the notification of the information based on a result of the second comparison.

13. A non-transitory computer-readable storage medium encoded with a computer-readable program that enables a computer to execute functions comprising:
at a first time, setting a first value of a tolerable amount of the physical condition of the subject; and
after the first time:
  controlling one or more sensors to receive signals output from the sensors and, based on the received signals, to:
    acquire a plurality of values of bio-information relating to bodily functions of a subject over time;
    acquire a plurality of values of activity information relating to activity of the subject over time; and
    acquire a plurality of values of environmental information relating to an environment around the subject over time;
  estimating a remaining amount of a physical condition of the subject based on the plurality of values of bio-information the plurality of values of activity information, and the plurality of values of environmental information;
  at a second time after the first time, determining whether there is a change in an intensity of one or more of the plurality of values of the bio-information, the plurality of values of the activity information, and the plurality of values of the environmental information over time;
  in response to determining that there is no change in the intensity of the plurality of values of the bio-information, the plurality of values of the activity information and the plurality of values of the environmental information over time:
    performing a first comparison of the remaining amount of the physical condition to the first value of the tolerable amount of the physical condition; and
    determining whether to perform a notification of information based on a result of the first comparison; and
  in response to determining that there is a change in the intensity of one or more of the plurality of values of the bio-information, the plurality of values of the activity information, and the plurality of values of the environmental information over time:
    correcting the tolerable amount of the physical condition from the first value to a second value;
    performing a second comparison of the remaining amount of the physical condition to the second value of the tolerable amount of the physical condition; and
    determining whether to perform the notification of the information based on a result of the second comparison.

\* \* \* \* \*

UNITED STATES PATENT AND TRADEMARK OFFICE
CERTIFICATE OF CORRECTION

| | | |
|---|---|---|
| PATENT NO. | : 11,030,911 B2 | Page 1 of 1 |
| APPLICATION NO. | : 15/427256 | |
| DATED | : June 8, 2021 | |
| INVENTOR(S) | : Kazunori Kita | |

It is certified that error appears in the above-identified patent and that said Letters Patent is hereby corrected as shown below:

On the Title Page

Item [56], Page 2 should read:
JP 2015-189470 11/2015

In the Claims

Column 19, Claim 1, Line 12 should read:
bio-information, the plurality of values of activity Column 22, Claim 13, Line 3 should read:
bio-information, the plurality of values of activity Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*